(12) United States Patent
Stark et al.

(10) Patent No.: US 8,946,121 B2
(45) Date of Patent: Feb. 3, 2015

(54) ANTIFUNGAL COMPOSITIONS

(75) Inventors: Jacobus Stark, Echt (NL); Angelique De Rijk, Echt (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 13/985,452

(22) PCT Filed: Mar. 1, 2012

(86) PCT No.: PCT/EP2012/053509
§ 371 (c)(1),
(2), (4) Date: Aug. 14, 2013

(87) PCT Pub. No.: WO2012/117051
PCT Pub. Date: Sep. 7, 2012

(65) Prior Publication Data
US 2013/0324403 A1    Dec. 5, 2013

(30) Foreign Application Priority Data

Mar. 3, 2011 (EP) .................................. 11156773

(51) Int. Cl.
*A01N 43/90* (2006.01)
*A01N 43/653* (2006.01)
*A01N 55/10* (2006.01)
*A23L 3/34* (2006.01)

(52) U.S. Cl.
CPC .............. *A01N 43/90* (2013.01); *A01N 43/653* (2013.01); *A23L 3/34* (2013.01)
USPC ............... 504/101; 504/100; 514/31; 514/63; 514/266.23; 514/383; 514/384; 426/335; 426/532

(58) Field of Classification Search
USPC ......... 504/100, 101; 514/31, 63, 266.23, 383, 514/384; 426/335, 532
See application file for complete search history.

(56) References Cited

U.S. PATENT DOCUMENTS

| 6,156,362 A | * | 12/2000 | Cirigliano et al. | ............. 426/335 |
| 7,816,332 B2 | * | 10/2010 | Stark et al. | ....................... 514/31 |
| 2005/0226974 A1 | * | 10/2005 | Faragher et al. | .............. 426/335 |

FOREIGN PATENT DOCUMENTS

| EP | 0101102 A2 | 2/1984 |
| EP | 0748588 A1 | 12/1996 |
| EP | 0986965 A1 | 3/2000 |
| EP | 2036438 A1 | 3/2009 |
| WO | 2007009969 A2 | 1/2007 |

OTHER PUBLICATIONS

International Search Report for PCT/EP2012/053509, Mailed May 18, 2012.

* cited by examiner

*Primary Examiner* — John Pak
(74) *Attorney, Agent, or Firm* — Miles & Stockbridge, PC

(57) ABSTRACT

The present invention relates to new antifungal compositions and their use in the treatment of agricultural products.

12 Claims, No Drawings

US 8,946,121 B2

ANTIFUNGAL COMPOSITIONS

CROSS REFERENCE TO RELATED APPLICATIONS

This application is a §371 National Stage Application of PCT/EP2012/053509, filed Mar. 1, 2012, which claims priority to European Application No. 11156773.1, filed Mar. 3, 2011.

BACKGROUND OF THE INVENTION

1. Field of the Invention

The present invention discloses new antimicrobial compositions to control plant diseases and to prevent microbial spoilage of crops.

2. Description of Related Art

It is estimated that about 25% of the world crop production is lost due to microbial spoilage, of which spoilage by fungi is by far the most important cause. Not only from an economical point of view, but also from a humane point of view it is of great importance to prevent spoilage of food products. After all, in many parts of the world people suffer from hunger.

Success in combating plant and crop diseases and in reducing the damage they cause to yields and quality depends greatly on the timely application of fungicides. The prolonged and frequent use of many fungicides such as e.g. benzamidazoles has contributed to reduce their effectiveness thanks to the development of phenomena of resistance.

An important group of fungicides are the triazoles. The first triazole that was introduced was triadimefon. This triazole was introduced in 1976 by Bayer (see Kuck et al., 1987). Triadimefon provided curative as well as protective activity, low application rates and excellent redistribution in the plant. Additional triazole fungicides were introduced over the next two decades with improved potency and plant safety (e.g., epoxiconazole), a broader effective spectrum (e.g., propiconazole, tebuconazole) or specialized applications (e.g., difenoconazole and triticonazole for seed treatment) (see Kuck et al., 1987). Next to their use in protecting agricultural products such as harvested fruit or vegetables from phytopathogenic fungi (see EP 2 036 438 A1) or cereals from mycotoxin contamination (see WO 2007/009969), triazoles have been used to protect food products from fungal decay (see EP 0 101 102 A2).

Triazole fungicides however have not been immune to challenges in their development and maintenance. They have well-documented side effects on plants. Application to shoots and roots often reduces elongation and causes leaves to be smaller, thicker, and greener. Treated plants may be delayed in senescence, which can impede harvest or improve yields, depending on the crop (see Buchenauer, 1987).

A larger concern has been resistance development, since triazole fungicides have many of the same properties as the benzimidazoles. Resistance to the triazole fungicides developed first in the powdery mildews and has also been observed on other diseases (see Kuck et al., 1987; Buchenauer, 1987; Ma et al., 2002).

Moreover, although the launch of triazole fungicides provided potent, systemic fungicide solutions for Ascomycete and Basidiomycete diseases, control of devastating Oomycete diseases such as potato late blight and grape downy mildew is limited and root rots of established plants (caused by *Phytophthora* and *Pythium*) and systemic downy mildews cannot be controlled at all by applying triazole fungicides.

For many decades, the polyene macrolide antimycotic natamycin has been used to prevent fungal growth on food products such as cheeses and sausages. For instance, in EP 0 748 588 A1 the use of fungal compositions comprising a polyene antifungal agent and an imidazole antifungal agent for the treatment of food and agricultural products is described. This natural preservative, which is produced by fermentation using *Streptomyces natalensis*, is widely used throughout the world as a food preservative and has a long history of safe use in the food industry. It is very effective against all known food spoilage fungi. Although natamycin has been applied for many years in e.g. the cheese industry, up to now development of resistant fungal species has never been observed.

Consequently, it can be concluded that there is a severe need for more effective antimicrobial compositions, e.g. antifungal compositions, for the treatment of fungal growth in and on plants and crops.

SUMMARY

The present invention solves the problem by providing a new synergistic antimicrobial, e.g. antifungal, composition comprising a polyene antifungal compound and at least one antifungal compound from the family of triazole fungicides. As used herein, the term "synergistic" means that the combined effect of the antifungal compounds when used in combination is greater than their additive effects when used individually.

DETAILED DESCRIPTION OF A PREFERRED EMBODIMENT

In general, synergistic activity of two active ingredients can be tested in for example the analysis of variance model using the treatment interaction stratum (see Slinker, 1998). Relative efficacy can be calculated by means of the following formula: ((value of evolution status of untreated control−value of evolution status of composition)/(value of evolution status of untreated control))*100. An interaction coefficient can then be calculated by means of the following formula: ((relative efficacy of combination compound A+compound B)/(relative efficacy of compound A+relative efficacy of compound B))*100. An interaction coefficient larger than 100 indicates synergy between the compounds.

Alternatively, synergy can be calculated as follows: the antifungal activity (in %) of the individual active ingredients can be determined by calculating the reduction in mould growth observed on products treated with the active ingredients in comparison to the mould growth on products treated with a control composition. The expected antifungal activity (E in %) of the combined antifungal composition comprising both active ingredients can be calculated according to the Colby equation (Colby, 1967): $E = X + Y - [(X \cdot Y)/100]$, wherein X and Y are the observed antifungal activities (in %) of the individual active ingredients X and Y, respectively. If the observed antifungal activity (O in %) of the combination exceeds the expected antifungal activity (E in %) of the combination and the synergy factor O/E is thus >1.0, the combined application of the active ingredients leads to a synergistic antifungal effect.

In an embodiment of the invention, the at least one antifungal compound from the family of triazole fungicides is selected from the group consisting of amisulbrom, azaconazole, bitertanol, bromuconazole, cyproconazole, diclobutrazol, difenoconazole, diniconazole, diniconazole-M, epoxiconazole, etaconazole, fenbuconazole, fluotrimazole, fluquinconazole, flusilazole, flutriafol, furconazole, furconazole-cis, hexaconazole, huanjunzuo, imibenconazole, ipconazole, metconazole, myclobutanil, penconazole, propiconazole, prothioconazole, quinconazole, simeconazole, tebuconazole, tetraconazole, triazbutil, triticonazole, uniconazole and uniconazole-P. In a preferred embodiment the at least one antifungal compound from the family of triazole fungicides is selected from the group consisting of bitertanol, cyproconazole, difenoconazole, epoxiconazole, fenbuconazole, fluquinconazole, flusilazole, flutriafol, metconazole, myclobutanil, propiconazole, prothioconazole, tebuconazole, tetraconazole, triticonazole and uniconazole. In an even more preferred embodiment the at least one antifungal compound from the family of triazole fungicides is selected from the group consisting of difenoconazole, epoxiconazole, fluquinconazole, flusilazole, flutriafol, propiconazole, prothioconazole, tebuconazole and tetraconazole. In an embodiment the compositions may also contain two or more different antifungal compounds from the family of triazole fungicides. It is to be understood that derivatives of antifungal compounds from the family of triazole fungicides including, but not limited to, salts or solvates of antifungal compounds from the family of triazole fungicides or modified forms of antifungal compounds from the family of triazole fungicides may also be applied in the compositions of the invention. Examples of commercial products containing triazole fungicides such as propiconazole are the products with the brand name Tilt® (propiconazole), Propimax® (propiconazole), Bumper® (propiconazole), Quilt® (propiconazole+azoxystrobin) or Stratego® (propiconazole+trifloxystrobin). Examples of commercial products containing triazole fungicides such as tebuconazole are the products with the brand name Folicur® (tebuconazole), Orius® (tebuconazole), Uppercut® (tebuconazole) or Headline SBR® (tebuconazole+pyraclostrobin). Examples of commercial products containing triazole fungicides such as tetraconazole, metconazole or prothioconazole are the products with the brand name Domark® (tetraconazole), Twinline® (metconazole+pyraclostrobin) or Stratego YLD® (prothioconazole+trifloxystrobin) or Proline® (prothioconazole), respectively. Said commercial products can be incorporated in the present invention.

In an embodiment the polyene antifungal compound is selected from the group consisting of natamycin, nystatin, amphotericin B, trienin, etruscomycin, filipin, chainin, dermostatin, lymphosarcin, candicidin, aureofungin A, aureofungin B, hamycin A, hamycin B and lucensomycin. In a preferred embodiment the polyene antifungal compound is natamycin. In an embodiment the compositions may also contain two or more different polyene antifungal compounds. It is to be understood that derivatives of polyene antifungal compounds including, but not limited to, salts or solvates of polyene antifungal compounds or modified forms of polyene antifungal compounds may also be applied in the compositions of the invention. Examples of commercial products containing natamycin are the products with the brand name Delvocid®. Such products are produced by DSM Food Specialties (The Netherlands) and may be solids containing e.g. 50% (w/w) natamycin or liquids comprising between e.g. 2-50% (w/v) natamycin. Said commercial products can be incorporated in the compositions of the invention.

The composition of the present invention generally comprises from about 0.005 g/l to about 100 g/l and preferably from about 0.01 g/l to about 50 g/l of a polyene antifungal compound. Preferably, the amount is from 0.01 g/l to 3 g/l.

The composition of the present invention generally comprises from about 0.0001 g/l to about 2000 g/l and preferably from about 0.0005 g/l to about 1500 g/l of an antifungal compound from the family of triazole fungicides. More preferably, the amount is from 0.001 g/l to 1000 g/l.

In an embodiment the composition of the present invention further comprises at least one additional compound selected from the group consisting of a sticking agent, a carrier, a colouring agent, a protective colloid, an adhesive, a herbicide, a fertilizer, a thickening agent, a sequestering agent, a thixotropic agent, a surfactant, a further antimicrobial compound, a detergent, a preservative, a spreading agent, a filler, a spray oil, a flow additive, a mineral substance, a solvent, a dispersant, an emulsifier, a wetting agent, a stabiliser, an antifoaming agent, a buffering agent, an UV-absorber and an antioxidant. A further antimicrobial antifungal compound may be an antifungal compound (e.g. imazalil, thiabendazole or chlorthalonil) or a compound to combat insects, nematodes, mites and/or bacteria. Of course, the compositions according to the invention may also comprise two or more of any of the above additional compounds. Any of the above mentioned additional compounds may also be combined with the polyene antifungal compound and/or the at least one antifungal compound from the family of triazole fungicides in case the antifungal compounds are applied separately. In an embodiment the additional compounds are additives acceptable for the specific use, e.g. food, feed, medicine, cosmetics or agriculture. Additional compounds suitable for use in food, feed, medicine, cosmetics or agriculture are known to the person skilled in the art.

In a specific embodiment the further antimicrobial compound is a natural crop protection compound belonging to the group of phosphites, e.g. $KH_2PO_3$ or $K_2HPO_3$ or a mixture of both phosphite salts. Phosphite containing compounds as used herein means compounds comprising a phosphite group, i.e. $PO_3$ (in the form of e.g. $H_2PO_3^-$, $HPO_3^{2-}$ or $PO_3^{3-}$) or any compound which allows the release of a phosphite ion including compounds such as phosphorous acid and phosphonic acid as well as derivatives thereof such as esters and/or alkali metal or alkaline earth metal salts thereof. In case the compositions of the present invention comprise a polyene antifungal compound (e.g. natamycin) and at least one phosphite containing compound, they preferably comprise 0.1 g or less lignosulphonate, more preferably 0.1 g or less polyphenol, per gram polyene antifungal compound. Preferably, they comprise 0.01 g or less lignosulphonate, more preferably 0.01 g or less polyphenol, per gram polyene antifungal compound. In particular, they are free of lignosulphonate and preferably free of polyphenol. Suitable examples of phosphite containing compounds are phosphorous acid and its (alkali metal or alkaline earth metal) salts such as potassium phosphites e.g. $KH_2PO_3$ and $K_2HPO_3$, sodium phosphites and ammonium phosphites, and $(C_1-C_4)$ alkyl esters of phosphorous acid and their salts such as aluminum ethyl phosphite (fosetyl-Al), calcium ethyl phosphite, magnesium isopropyl phosphite, magnesium isobutyl phosphite, magnesium sec-butyl phosphite and aluminum N-butyl phosphite. Of course, mixtures of phosphite containing compounds are also encompassed. A mixture of e.g. $KH_2PO_3$ and $K_2HPO_3$ can easily be obtained by e.g. adding KOH or $K_2CO_3$ to a final pH of 5.0-6.0 to a $KH_2PO_3$ solution. As indicated above, precursor-type compounds which in the crop or plant are metabolized into phosphite compounds can also be included in the compositions of the present invention. Examples are phosphonates such as the fosetyl-aluminium complex. In e.g. a crop or plant the ethyl phosphonate part of this molecule is metabolized into a phosphite. An example of such a compound in the commercial ethyl hydrogen phosphonate product called Aliette® (Bayer, Germany). The ratio of phosphite to natamycin (in weight) in the compositions is in general between 2:1 to 500:1 (w/w), preferably between 3:1 to 300:1 (w/w) and more preferably between 5:1 to 200:1 (w/w).

Compositions according to the invention may have a pH of from 1 to 10, preferably of from 2 to 9, more preferably of from 3 to 8 and most preferably of from 4 to 7. They may be solid, e.g. powder compositions, or may be liquid. The compositions of the present invention can be aqueous or non-aqueous ready-to-use compositions, but may also be aqueous or non-aqueous concentrated compositions/suspensions or stock compositions, suspensions and/or solutions which before use have to be diluted with a suitable diluent such as water or a buffer system. Alternatively, the compositions of the invention can also be used to prepare coating emulsions. The compositions of the present invention can also have the form of concentrated dry products such as e.g. powders, granulates and tablets. They can be used to prepare compositions for immersion or spraying of products such as agricultural products including plants, crops, vegetables and/or fruits. Of course, the above is also applicable when the polyene antifungal compound and the at least one antifungal compound from the family of triazole fungicides are applied as separate compositions.

In a further aspect the invention relates to a kit comprising a polyene antifungal compound and at least one antifungal compound from the family of triazole fungicides. The polyene antifungal compound and the at least one antifungal compound from the family of triazole fungicides may be present in two separate packages, e.g. containers. The components of the kit may be either in dry form or liquid form in the package. If necessary, the kit may comprise instructions for dissolving the compounds. In addition, the kit may contain instructions for applying the compounds.

In a further aspect the invention pertains to a method for protecting a product against fungi by treating the agricultural product with a polyene antifungal compound and at least one antifungal compound from the family of triazole fungicides. In addition, the product can be treated with other antifungal and/or antimicrobial compounds either prior to, concomitant with or after treatment of the products with the polyene antifungal compound and the at least one antifungal compound from the family of triazole fungicides. The product may be treated by sequential application of the polyene antifungal compound and the at least one antifungal compound from the family of triazole fungicides or vice versa. Alternatively, the product may be treated by simultaneous application of the polyene antifungal compound and the at least one antifungal compound from the family of triazole fungicides. In case of simultaneous application, the compounds can be present in different compositions that are applied simultaneously or the compounds may be present in a single composition. In yet another embodiment the product may be treated by separate or alternate modes of applying the antifungal compounds. In an embodiment the invention is directed to a process for the treatment of products by applying the polyene antifungal compound and the at least one antifungal compound from the family of triazole fungicides to the products. By applying the compounds fungal growth on or in the products can be prevented. In other words, the compounds protect the products from fungal growth and/or from fungal infection and/or from fungal spoilage. The compounds can also be used to treat products that have been infected with a fungus. By applying the compounds the disease development due to fungi on or in these products can be slowed down, stopped or the products may even be cured from the disease. In an embodiment of the invention the products are treated with a composition or kit according to the invention. In an embodiment the product is a food, feed, pharmaceutical, cosmetic or agricultural product. In a preferred embodiment the product is an agricultural product.

The polyene antifungal compound and the at least one antifungal compound from the family of triazole fungicides, the compositions according to the invention and the kits according to the invention can be applied to the products by spraying. Other methods suitable for applying these compounds, compositions and kits in liquid form to the products are also a part of the present invention. These include, but are not limited to, dipping, watering, drenching, introduction into a dump tank, vaporizing, atomizing, fogging, fumigating, painting, brushing, dusting, foaming, spreading-on, packaging and coating (e.g. by means of wax or electrostatically). In addition, the antifungal compounds may also be injected into the soil. Spraying applications using automatic systems are known to reduce the labour costs and are cost-effective. Methods and equipment well-known to a person skilled in the art can be used for that purpose. The compositions according to the invention can be regularly sprayed, when the risk of infection is high. When the risk of infection is lower spray intervals may be longer. Depending on the type of application, the amount of polyene antifungal compound applied may vary from 5 ppm to 10,000 ppm, preferably from 10 ppm to 5,000 ppm and most preferably from 20 to 1,000 ppm. Depending on the type of application, the amount of the at least one antifungal compound from the family of triazole fungicides applied may vary from 10 ppm to 5,000 ppm, preferably from 20 ppm to 3,000 ppm and most preferably from 50 to 1,000 ppm.

In a specific embodiment the agricultural product can be treated post-harvest. By using a polyene antifungal compound and the at least one antifungal compound from the family of triazole fungicides the control of post-harvest and/or storage diseases is achieved for a long period of time to allow transport of the harvested agricultural product over long distances and under various storage conditions with different controlled atmosphere systems in respect of temperature and humidity. Post-harvest storage disorders are e.g. lenticel spots, scorch, senescent breakdown, bitter pit, scald, water core, browning, vascular breakdown, $CO_2$ injury, $CO_2$ or $O_2$ deficiency, and softening. Fungal diseases may be caused for example by the following fungi: *Mycosphaerella* spp., *Mycosphaerella musae*, *Mycosphaerella fragariae*, *Mycosphaerella citri*; *Mucor* spp., e.g. *Mucor piriformis*; *Monilinia* spp., e.g. *Monilinia fructigena*, *Monilinia laxa*; *Phomopsis* spp., *Phomopsis natalensis*; *Colletotrichum* spp., e.g. *Colletotrichum musae*, *Colletotrichum gloeosporioides*, *Colletotrichum coccodes*; *Verticillium* spp., e.g. *Verticillium theobromae*; *Nigrospora* spp.; *Botrytis* spp., e.g. *Botrytis cinerea*; *Dipodia* spp., e.g. *Dipodia citri*; *Pezicula* spp.; *Alternaria* spp., e.g. *Alternaria citri*, *Alternaria alternata*; *Septoria* spp., e.g. *Septoria depressa*; *Venturia* spp., e.g. *Venturia inaequalis*, *Venturia pyrina*; *Rhizopus* spp., e.g. *Rhizopus stolonifer*, *Rhizopus oryzae*; *Glomerella* spp., e.g. *Glomerella cingulata*; *Sclerotinia* spp., e.g. *Sclerotinia fruiticola*; *Ceratocystis* spp., e.g. *Ceratocystis paradoxa*; *Fusarium* spp., e.g. *Fusarium semitectum*, *Fusarium moniliforme*, *Fusarium solani*, *Fusarium oxysporum*; *Cladosporium* spp., e.g. *Cladosporium fulvum*, *Cladosporium cladosporioides*, *Cladosporium cucumerinum*, *Cladosporium musae*; *Penicillium* spp., e.g. *Penicillium funiculosum*, *Penicillium expansum*, *Penicillium digitatum*, *Penicillium italicum*; *Phytophthora* spp., e.g. *Phytophthora citrophthora*, *Phytophthora fragariae*, *Phytophthora cactorum*, *Phytophthora parasitica*; *Phacydiopycnis* spp., e.g. *Phacydiopycnis malirum*; *Gloeosporium* spp., e.g. *Gloeosporium album*, *Gloeosporium*

*perennans, Gloeosporium fructigenum, Gloeosporium singulata; Geotrichum* spp., e.g. *Geotrichum candidum; Phlyctaena* spp., e.g. *Phlyctaena vagabunda; Cylindrocarpon* spp., e.g. *Cylindrocarpon mali; Stemphyllium* spp., e.g. *Stemphyllium vesicarium; Thielaviopsis* spp., e.g. *Thielaviopsis paradoxy; Aspergillus* spp., e.g. *Aspergillus niger, Aspergillus carbonarius; Nectria* spp., e.g. *Nectria galligena; Cercospora* spp., e.g. *Cercospora angreci, Cercospora apii, Cercospora atrofiliformis, Cercospora musae, Cercospora zeae-maydis.*

Another aspect of the present invention relates to the use of a polyene antifungal compound and at least one antifungal compound from the family of triazole fungicides to protect a product against fungi. As indicated above, the compounds may be used, e.g. applied, sequentially or simultaneously. In an embodiment the invention relates to a use, wherein a composition or kit according to the invention is applied to the product. In an embodiment the product is a food, feed, pharmaceutical, cosmetic or agricultural product. In a preferred embodiment the product is an agricultural product.

In a specific embodiment the polyene antifungal compound and at least one antifungal compound from the family of triazole fungicides can be used in medicine, e.g. to treat and/or prevent fungal diseases. The polyene antifungal compound and at least one antifungal compound from the family of triazole fungicides can for instance be used in the form of a pharmaceutical composition. The composition may further comprise pharmaceutically acceptable excipients. The antifungal compounds may be administered orally or parenterally. The type of composition is dependent on the route of administration.

A further aspect of the invention is directed to a product treated with a polyene antifungal compound and at least one antifungal compound from the family of triazole fungicides. In an embodiment the product is treated with a composition or kit according to the invention. The invention is therefore directed to a product comprising a polyene antifungal compound and at least one antifungal compound from the family of triazole fungicides. The treated products may comprise a polyene antifungal compound and at least one antifungal compound from the family of triazole fungicides on their surface and/or inside the product. Alternatively, the treated products may comprise a coating comprising these compounds. In an embodiment the treated products comprise from 0.000001 to 200 mg/dm$^2$, preferably 0.00001 to 100 mg/dm$^2$, more preferably from 0.00005 to 10 mg/dm$^2$ of the polyene antifungal compound on their surface. In a further embodiment they comprise from 0.000001 to 200 mg/dm$^2$, preferably 0.00001 to 100 mg/dm$^2$, more preferably from 0.00005 to 10 mg/dm$^2$ of the at least one antifungal compound from the family of triazole fungicides on their surface. In an embodiment the product is a food, feed, pharmaceutical, cosmetic or agricultural product. In a preferred embodiment the product is an agricultural product.

The term "food products" as used herein is to be understood in a very broad sense and includes, but is not limited to, cheese, cream cheese, shredded cheese, cottage cheese processed cheese, sour cream, dried fermented meat product including salamis and other sausages, wine, beer, yoghurt, juice and other beverages, salad dressing, cottage cheese dressing, dips, bakery products and bakery fillings, surface glazes and icing, spreads, pizza toppings, confectionery and confectionery fillings, olives, olive brine, olive oil, juices, tomato purees and paste, condiments, and fruit pulp and the like food products.

The term "feed products" as used herein is also to be understood in a very broad sense and includes, but is not limited to, pet food, broiler feed, etc.

The term "pharmaceutical product" as used herein is also to be understood in a very broad sense and includes products comprising an active molecule such as a drug, agent, or pharmaceutical compound and optionally a pharmaceutically acceptable excipient, i.e. any inert substance that is combined with the active molecule for preparing an agreeable or convenient dosage form.

The term "cosmetic product" as used herein is also to be understood in a very broad sense and includes products that are used for protecting or treating horny tissues such as skin and lips, hair and nails from drying by preventing transpiration of moisture thereof and further conditioning the tissues as well as giving good appearance to these tissues. Products contemplated by the term "cosmetic product" include, but are not limited to, moisturizers, personal cleansing products, occlusive drug delivery patches, nail polish, powders, wipes, hair conditioners, skin treatment emulsions, shaving creams and the like.

The term "agricultural products" as used herein is also to be understood in a very broad sense and includes, but is not limited to, cereals, e.g. wheat, barley, rye, oats, rice, sorghum and the like; beets, e.g. sugar beet and fodder beet; pome and stone fruit and berries, e.g. apples, pears, plums, apricots, peaches, almonds, cherries, strawberries, raspberries and blackberries; leguminous plants, e.g. beans, lentils, peas, soy beans; oleaginous plants, e.g. rape, mustard, poppy, olive, sunflower, coconut, castor-oil plant, cocoa, ground-nuts; cucurbitaceae, e.g. pumpkins, gherkins, melons, cucumbers, squashes, aubergines; fibrous plants, e.g. cotton, flax, hemp, jute; citrus fruit, e.g. oranges, lemons, grapefruits, mandarins, limes; tropical fruit, e.g. papayas, passion fruit, mangos, carambolas, pineapples, bananas, kiwis; vegetables, e.g. spinach, lettuce, asparagus, brassicaceae such as cabbages and turnips, carrots, onions, tomatoes, potatoes, seed-potatoes, hot and sweet peppers; laurel-like plants, e.g. avocado, cinnamon, camphor tree; or products such as maize, tobacco, nuts, coffee, sugarcane, tea, grapevines, hops, rubber plants, as well as ornamental plants, e.g. cut flowers, roses, tulips, lilies, narcissus, crocuses, hyacinths, dahlias, gerbera, carnations, fuchsias, chrysanthemums, and flower bulbs, shrubs, deciduous trees and evergreen trees such as conifers, plants and trees in greenhouses. It includes, but is not limited to, plants and their parts, fruits, seeds, cuttings, cultivars, grafts, bulbs, tubers, root-tubers, rootstocks, cut flowers and vegetables.

A method for preparing a composition as described herein is another aspect of the present invention. The method comprises adding a polyene antifungal compound to at least one antifungal compound from the family of triazole fungicides. The compounds may for instance be added separately to an aqueous composition and mixed, followed, if necessary, by adjustment of the pH, viscosity, etc. If added separately, some or all of the separate compounds may be in powder form, but alternatively some or all may also be in liquid form. The compounds may for instance also be added to one another in powder form and mixed to obtain a powdered composition. The powdered composition may then be added to an aqueous composition.

EXAMPLE 1

Pre-harvest Application

Leaves of banana plants are inoculated with fungi. As a control non-inoculated leaves are also included. Next, a defined part of the leaves are treated with composition 1 (natamycin), composition 2 (bitertanol), composition 3 (cyproconazole), composition 4 (difenoconazole), composition 5 (fenbuconazole), composition 6 (flusilazole), composition 7 (flutriafol), composition 8 (metconazole), composition 9 (myclobutanil), composition 10 (propiconazole), composition 11 (prothioconazole), composition 12 (tebuconazole), composition 13 (tetraconazole), composition 14 (triticonazole), composition 15 (uniconazole), composition 16 (natamycin+bitertanol), composition 17 (natamycin+ cyproconazole), composition 18 (natamycin+difenoconazole), composition 19 (natamycin+fenbuconazole), composition 20 (natamycin+flusilazole), composition 21 (natamycin+flutriafol), composition 22 (natamycin+metconazole), composition 23 (natamycin+myclobutanil), composition 24 (natamycin+propiconazole), composition 25 (natamycin+prothioconazole), composition 26 (natamycin+ tebuconazole), composition 27 (natamycin+tetraconazole), composition 28 (natamycin+triticonazole) and composition 29 (natamycin+uniconazole). Each composition is applied by spraying. Untreated leaves are also included (untreated control).

The obtained results show that the compositions of the present invention protect banana plants from fungal growth and further demonstrate that the compositions of the present invention show a synergistically enhanced activity compared to the activity of the active compounds when applied individually.

EXAMPLE 2

Post-harvest Application

Bananas are injured according to the method described by de Lapeyre de Bellaire and Dubois (1987). Bananas are wounded using a cork borer followed by contamination with fungal spores. After incubation for several hours at room temperature, the bananas are dipped in one of the following compositions: a) no treatment (control 1), b) dipped in water (control 2), c) dipped in natamycin, d) dipped in bitertanol, e) dipped in cyproconazole, f) dipped in difenoconazole, g) dipped in fenbuconazole, h) dipped in flusilazole, i) dipped in flutriafol, j) dipped in metconazole, k) dipped in myclobutanil, l) dipped in propiconazole, m) dipped in prothioconazole, n) dipped in tebuconazole, o) dipped in tetraconazole, p) dipped in triticonazole, q) dipped in uniconazole, r) dipped in natamycin+bitertanol, s) dipped in natamycin+cyproconazole, t) dipped in natamycin+difenoconazole, u) dipped in natamycin+fenbuconazole, v) dipped in natamycin+flusilazole, w) dipped in natamycin+flutriafol, x) dipped in natamycin+metconazole, y) dipped in natamycin+myclobutanil, z) dipped in natamycin+propiconazole, z1) dipped in natamycin+prothioconazole, z2) dipped in natamycin+tebuconazole, z3) dipped in natamycin+tetraconazole, z4) dipped in natamycin+triticonazole, z5) dipped in natamycin+uniconazole. After this treatment the bananas are incubated in closed boxes at 21° C. at elevated humidity. Each day the bananas are judged visually on fungal development.

The results show that the composition comprising natamycin and at least one antifungal compound from the family of triazole fungicides protects bananas better against fungi than natamycin or at least one antifungal compound from the family of triazole fungicides alone. Surprisingly, the combined application of natamycin and at least one antifungal compound from the family of triazole fungicides leads to a strong synergistic reduction in infection.

EXAMPLE 3

Treatment of Bananas

Four organic, unripe (green) bananas were used per treatment. The peel of each banana was wounded thrice using a cork borer according to the method described by de Lapeyre de Bellaire and Dubois (1987). Subsequently, each wound was inoculated with 15 µl of a *Fusarium proliferatum* suspension containing $1 \times 10^5$ of spores/ml. After incubation for 4 hours at 20° C., each banana wound was treated with 100 µl of a freshly prepared aqueous antifungal composition comprising either 500 ppm natamycin (DSM Food Specialties, Delft, The Netherlands), 1000 ppm propiconazole or both. In addition, the antifungal compositions comprised 1.00% (w/w) methylhydroxyethylcellulose (MHEC), 0.40% (w/w) xanthan gum, 0.20% (w/w) anti-foaming agent, 0.30% (w/w) citric acid, 0.39% (w/w) lactic acid and 0.11% (w/w) potassium sorbate. The pH of the composition was 4.0. A composition without natamycin or propiconazole was used as control. The treated, unripe bananas were incubated in a closed box in the dark at 20° C. and a relative air humidity of 95%, which was obtained in the presence of a saturated $Na_2HPO_4$ aqueous solution. During the first 20 days of incubation, a ripe (yellow) banana was included in the closed box to elevate the ethylene gas level and thus induce ripening of the treated, unripe bananas.

The degree of mould growth on the bananas was determined by counting the number of moulded wounds per total of 12 wounds after 39 and 42 days of incubation.

The results in Table 1 clearly demonstrate that the antifungal composition comprising both 500 ppm natamycin and 1000 ppm propiconazole protected bananas better against mould growth than natamycin or propiconazole alone.

After 39 and 42 days of incubation, all 12 wounds treated with either the control composition or natamycin alone were moulded, as were 4 of the 12 wounds treated with propiconazole alone. However, when treated with the composition comprising both natamycin and propiconazole, none of the 12 wounds were moulded after 39 days and only 1 of the 12 wounds after 42 days (see Table 1).

Hence, the combination of 500 ppm natamycin and 1000 ppm propiconazole has synergistic antifungal activity on bananas.

EXAMPLE 4

Treatment of Bananas

The experiment was conducted as described in Example 3, except for the fact that each inoculated banana wound was treated with 100 µl of a freshly prepared aqueous antifungal composition comprising either 500 ppm natamycin (DSM Food Specialties, Delft, The Netherlands), 150 ppm propiconazole or both.

During incubation, the degree of mould growth on the bananas was assessed in a twofold manner: (i) the number of moulded wounds per total of 12 wounds was counted; and (ii) the antifungal activity (in %) of the individual active ingredients was determined by calculating the reduction in mould growth observed on the banana wounds treated with the antifungal composition in comparison to the mould growth on the banana wounds treated with the control composition. The expected antifungal activity (E in %) of the combined antifungal composition comprising both active ingredients was calculated according to the Colby equation (Colby, 1967):

$$E=X+Y-[(X \cdot Y)/100]$$

wherein X and Y are the observed antifungal activities (in %) of the individual active ingredients X and Y, respectively. If the observed antifungal activity (O in %) of the combination exceeds the expected antifungal activity (E in %) of the combination and the synergy factor O/E is thus >1.0, the combined application of the active ingredients leads to a synergistic antifungal effect.

The results in Table 2 (number of moulded wounds per total of 12 wounds) and Table 3 (antifungal activity) prove that the combined antifungal composition comprising 500 ppm natamycin and 150 ppm propiconazole was more effective in reducing mould growth on bananas than natamycin or propiconazole alone.

After 26 days of incubation, all 12 wounds treated with the control composition were moulded, as were 8 of the 12 wounds treated with natamycin alone and 9 of the 12 wounds treated with propiconazole alone. However, none of the 12 wounds treated with the composition comprising natamycin and propiconazole showed mould growth (see Table 2). In addition, the observed antifungal activity of the composition comprising both natamycin and propiconazole was 8% higher than the expected antifungal activity, which resulted in a synergy factor >1.0 (see Table 3).

After 27, 28, 29, 31 and 32 days of incubation, all 12 wounds treated with either the control composition or propiconazole alone were moulded, as were 8 of the 12 wounds treated with natamycin alone. However, when the composition comprising natamycin and propiconazole was used for treatment, mould growth was observed for none of the 12 wounds on days 27, 28 and 29 and only 1 of the 12 wounds on days 31 and 32 (see Table 2). Moreover, the observed antifungal activity of the active ingredient combination of natamycin and propiconazole exceeded the expected antifungal activity with 8% to 18% between 27 and 32 days of incubation and synergy factors >1.0 were obtained (see Table 3).

Hence, the combined application of 500 ppm natamycin and 150 ppm propiconazole synergistically reduces mould growth on bananas.

EXAMPLE 5

Treatment of Bananas

The experiment was conducted as described in Example 3, except for the fact that each inoculated banana wound was treated with 100 µl of a freshly prepared aqueous antifungal composition comprising either 250 ppm natamycin (DSM Food Specialties, Delft, The Netherlands), 500 ppm propiconazole or both. During incubation, the degree of mould growth on the banana wounds was assessed according to the two methods described in Example 4.

The results in Table 4 (number of moulded wounds per total of 12 wounds) and Table 5 (antifungal activity) reveal that the antifungal composition comprising 250 ppm natamycin as well as 500 ppm propiconazole was superior to the compositions comprising either natamycin alone or propiconazole alone in reducing mould growth on bananas.

After 34 and 36 days of incubation, mould growth was observed for all 12 wounds treated with either the control composition or natamycin alone and for 10 of the wounds treated with propiconazole alone. However, when treated with the active ingredient combination of natamycin and propiconazole, only 7 of the 12 wounds were moulded after 34 days and 8 of the 12 wounds after 36 days (see Table 4).

Furthermore, the observed antifungal activity of the composition comprising both natamycin and propiconazole exceeded the expected antifungal activity with 11% and 21% after 34 and 36 days of incubation, respectively. Consequently, synergy factors >1.0 were obtained (see Table 5).

After 39 and 42 days of incubation, the observed antifungal activity of the composition comprising natamycin and propiconazole was respectively 32 and 38% higher than the expected antifungal activity. Consequently, the synergy factor increased from 1.1 on day 34 to 1.8 on day 39 and 2.1 on day 42 (see Table 5).

In conclusion, the results of this example clearly demonstrate that the antifungal activity of the combination of 250 ppm natamycin and 500 ppm propiconazole is synergistic when applied on bananas.

EXAMPLE 6

Treatment of Bananas

The experiment was conducted as described in Example 3, except for the fact that each inoculated banana wound was treated with 100 µl of a freshly prepared aqueous antifungal composition comprising either 250 ppm natamycin (DSM Food Specialties, Delft, The Netherlands), 50 ppm propiconazole or both. The antifungal activity (in %) of the individual and combined active ingredients on the treated banana wounds was determined according to the method described in Example 4.

The results in Table 6 show that the antifungal composition comprising both 250 ppm natamycin and 50 ppm propiconazole had a stronger antifungal activity than natamycin or propiconazole individually.

After 23, 27 and 29 days of incubation, the actually observed antifungal activity of the active ingredient combination of natamycin and propiconazole was 8 to 18% higher than the expected antifungal activity, which resulted in synergy factors >1.0.

Hence, the results of this example clearly demonstrate the synergistic antifungal activity between 250 ppm natamycin and 50 ppm propiconazole on bananas.

EXAMPLE 7

Treatment of Bananas

The experiment was conducted as described in Example 3, except for the fact that each inoculated banana wound was treated with 100 µl of a freshly prepared aqueous antifungal composition comprising either 50 ppm natamycin (DSM Food Specialties, Delft, The Netherlands), 250 ppm propiconazole or both. The degree of mould growth on the banana wounds was assessed according to the two methods described in Example 4.

The results in Table 7 (number of moulded wounds per total of 12 wounds) and Table 8 (antifungal activity) show that the combined antifungal composition comprising 50 ppm natamycin and 250 ppm propiconazole protected bananas more effectively against mould growth on bananas than the compositions comprising natamycin or propiconazole alone.

After 29 days of incubation, all 12 wounds treated with either the control composition or with natamycin alone were moulded, as were 5 of the 12 wounds treated with propiconazole alone. However, none of the 12 wounds treated with the composition comprising natamycin and propiconazole showed mould growth (see Table 7). In addition, the observed antifungal activity of the composition comprising both natamycin and propiconazole was 7% higher than the expected antifungal activity, which resulted in a synergy factor >1.0 (see Table 8).

After 32 days of incubation, all 12 wounds treated with either the control composition or with natamycin alone were moulded, as were 8 of the 12 wounds treated with propiconazole alone. However, only 2 of the 12 wounds treated with the composition comprising natamycin and propiconazole showed mould growth (see Table 7). Furthermore, the observed antifungal activity of the composition comprising both natamycin and propiconazole was 7% higher than the expected antifungal activity and a synergy factor >1.0 was obtained (see Table 8).

After 34 days of incubation, all 12 wounds treated with either the control composition or with natamycin alone were moulded, as were 10 of the 12 wounds treated with propiconazole alone. However, only 4 of the 12 wounds treated with the composition comprising natamycin and propiconazole showed mould growth (see Table 7). In addition, the observed antifungal activity of the composition comprising both natamycin and propiconazole was 10% higher than the expected antifungal activity. Hence, the synergy factor exceeded 1.0 (see Table 8).

After 36, 39 and 42 days of incubation, all 12 wounds treated with either the control composition, natamycin alone or propiconazole alone were moulded. However, when the composition comprising both natamycin and propiconazole was applied on the wounds, mould growth was observed for only 5 of the 12 wounds on day 36, 8 of the 12 wounds on day 39 and 10 of the 12 wounds on day 42 (see Table 7). Moreover, the observed antifungal activity of the active ingredient combination of natamycin and propiconazole exceeded the expected antifungal activity with 10, 30 and 37% after 36, 39 and 42 days of incubation, respectively. Consequently, the synergy factor increased from 1.1 on day 29, 32 and 34 to 1.2 on day 36, 1.5 on day 39 and 1.8 on day 42 (see Table 8).

Thus, the combined application of 50 ppm natamycin and 250 ppm propiconazole leads to a surprisingly strong synergistic reduction in mould growth on bananas.

EXAMPLE 8

Treatment of Bananas

The experiment was conducted as described in Example 3, except for the fact that each inoculated banana wound was treated with 100 µl of a freshly prepared aqueous antifungal composition comprising 500 natamycin (DSM Food Specialties, Delft, The Netherlands), 250 prothioconazole or both. A composition without natamycin or prothioconazole was used as control. The degree of mould growth on the bananas was determined by counting the number of moulded wounds per total of 12 wounds after 27 and 29 days of incubation.

The results in Table 9 reveal that the composition comprising 500 natamycin and 250 ppm prothioconazole was more successful in limiting mould growth on bananas than natamycin or prothioconazole individually.

After 27, 28 and 29 days of incubation, all 12 wounds treated with the control composition showed mould growth. In addition, mould growth was observed for 8 of the wounds treated with natamycin alone and 10 of the wounds treated with prothioconazole alone. However, only 2 of the 12 wounds treated with the composition comprising natamycin and prothioconazole were moulded (see Table 9).

In conclusion, the active ingredient combination of 500 ppm natamycin and 250 ppm prothioconazole has synergistic antifungal activity on bananas.

EXAMPLE 9

Treatment of Bananas

The experiment was conducted as described in Example 3, except for the fact that each inoculated banana wound was treated with 100 µl of a freshly prepared aqueous antifungal composition comprising 250 natamycin (DSM Food Specialties, Delft, The Netherlands), 100 prothioconazole or both. A composition without natamycin or prothioconazole was used as control. The degree of mould growth was determined as described in Example 8.

The results in Table 10 demonstrate that the composition comprising 250 ppm natamycin and 100 ppm prothioconazole protected bananas better against mould growth than natamycin or prothioconazole individually.

After 27, 28 and 29 days of incubation, all 12 wounds treated with either the control composition or natamycin alone were moulded. Of the 12 wounds treated with prothioconazole alone, 11 wounds showed mould growth on day 27 and 12 on day 28 and 29. However, only 9 of the 12 wounds treated with the composition comprising natamycin and prothioconazole were moulded after 27, 28 and 29 days of incubation (see Table 10).

This example clearly shows that synergistic antifungal activity exists between 250 ppm natamycin and 100 ppm prothioconazole when applied as active ingredient combination on bananas.

EXAMPLE 10

Treatment of Strawberries

Twelve fresh, organic strawberries were used per treatment. Each strawberry was wounded with a 0.5 mm long cut and each wound was inoculated with 10 µl of a *Botrytis cinerea* suspension containing $1\times10^5$ of spores/ml. After a 2-hour incubation period at 20° C., each strawberry was dipped individually for 1 minute in a freshly prepared aqueous antifungal composition comprising either 250 ppm natamycin (DSM Food Specialties, Delft, The Netherlands), 500 ppm prothioconazole or both. The antifungal compositions also comprised 1.00% (w/w) methylhydroxyethylcellulose (MHEC), 0.40% (w/w) xanthan gum, 0.20% (w/w) antifoaming agent, 0.30% (w/w) citric acid, 0.39% (w/w) lactic acid and 0.11% (w/w) potassium sorbate. The pH of the composition was 4.0. A composition without natamycin or prothioconazole was used as control. The treated strawberries were incubated in a closed box in the dark at 20° C. for 3 days.

After 2 and 3 days of incubation, the mould growth on the strawberries was assessed in a twofold manner: (i) the number of moulded strawberries per total of 12 strawberries was counted; and (ii) the antifungal activity (in %) of the individual and combined active ingredients was determined by calculating the reduction in mould growth observed on the strawberries treated with the antifungal composition in comparison to the mould growth on the strawberries treated with the control composition according to the Colby method described in Example 4 (Colby, 1967).

The results in Table 11 (number of moulded strawberries per total of 12 strawberries) and Table 12 (antifungal activity) demonstrate that the antifungal composition comprising 250 ppm natamycin and 500 ppm prothioconazole had a stronger antifungal activity on strawberries than natamycin or prothioconazole alone.

After 2 days of incubation, all 12 strawberries treated with either the control composition or prothioconazole alone showed mould growth, whereas 10 of the 12 strawberries treated with natamycin alone were moulded. However, mould growth was observed only for 6 of the 12 strawberries treated with the composition comprising natamycin and prothioconazole (see Table 11). Furthermore, the observed antifungal activity of the composition comprising both natamycin and prothioconazole exceeded the expected antifungal activity with 14%, which resulted in a synergy factor >1.0 (see Table 12).

After 3 days of incubation, all 12 strawberries treated with either the control composition, natamycin alone or prothioconazole alone showed mould growth. However, only 8 of the 12 strawberries treated with the composition comprising natamycin and prothioconazole were moulded (see Table 11). In addition, the observed antifungal activity of the combined composition comprising natamycin and prothioconazole was 10% higher than the expected antifungal activity and a synergy factor >1.0 was obtained (see Table 12).

Hence, the combined application of 250 ppm natamycin and 500 ppm prothioconazole synergistically reduces mould growth on strawberries.

EXAMPLE 11

Treatment of Mandarins

Ten fresh, organic mandarins were used per treatment. The peel of each mandarin was wounded once using a cork borer according to the method described by de Lapeyre de Bellaire and Dubois (1987). Subsequently, each wound was inoculated with 10 µl of a *Penicillium italicum* suspension containing $1 \times 10^4$ of spores/ml. After incubation for 2 hours at 20° C., the mandarins were dipped individually for 1 minute in a freshly prepared aqueous antifungal composition comprising either 500 ppm natamycin (DSM Food Specialties, Delft, The Netherlands), 600 ppm prothioconazole or both. In addition, the antifungal compositions comprised 3.1% (w/w) beeswax, 0.76% (w/w) glycerol, 0.66% (w/w) polyoxyethylene sorbitan monostearate (Tween 60), 0.03% (w/w) methylhydroxyethylcellulose (MHEC), 0.02% (w/w) xanthan gum, 0.02% (w/w) anti-foaming agent, 0.15% (w/w) citric acid and 0.01% (w/w) potassium sorbate. The pH of the composition was 4.0. A composition without natamycin or prothioconazole was used as control.

The treated mandarins were incubated in a closed box in the dark at 20° C. and assessed on mould growth after 25, 28, 31 and 34 days of incubation. The antifungal activity (in %) of the individual and combined active ingredients was determined by calculating the reduction in mould growth observed on the mandarins treated with the antifungal composition in comparison to the mould growth on the mandarins treated with the control composition according to the Colby method (Colby, 1967) described in Example 4.

The results in Table 13 prove that the antifungal composition comprising 500 ppm natamycin and 600 ppm prothioconazole was superior to the compositions comprising natamycin or propiconazole alone in preventing mould growth on mandarins.

After 25, 28, 31 and 34 days of incubation, the observed antifungal activity of the composition comprising both natamycin and propiconazole was respectively 6, 12, 32 and 38% higher than the expected antifungal activity. Consequently, the synergy factor increased from 1.1 on day 25 to 1.4 on day 34 (see Table 13).

Thus, the combined application of 500 ppm natamycin and 600 ppm propiconazole synergistically reduces mould growth on mandarins.

EXAMPLE 12

Treatment of Mandarins

The experiment was conducted as described in Example 11, except for the fact that each wounded, inoculated mandarin was dipped individually for 1 minute in a freshly prepared aqueous antifungal composition comprising either 250 ppm natamycin (DSM Food Specialties, Delft, The Netherlands), 150 ppm prothioconazole or both. The antifungal activity (in %) of the individual and combined active ingredients on mandarins was assessed after 13, 16, 21, 26, 29 and 34 days of incubation according to the Colby method (Colby, 1967) described in Example 4.

The results (see Table 14) reveal that the antifungal composition comprising 250 ppm natamycin and 150 ppm prothioconazole was more effective in reducing mould growth on mandarins than natamycin or prothioconazole alone.

After 13, 16, 21, 26, 29 and 34 of incubation, the observed antifungal activity of the active ingredient combination of natamycin and prothioconazole exceeded the expected antifungal activity with respectively 10, 15, 17, 28, 35 and 38%. The synergy factor increased from 1.1 on day 13 to 2.4 on day 34 (see Table 14).

It can therefore be concluded that the combined application of 250 ppm natamycin and 150 ppm prothioconazole leads to a synergistic reduction in mould growth on mandarins.

EXAMPLE 13

In vitro Antifungal Activity

To demonstrate synergistic antifungal activity of the combination of natamycin with propiconazole or prothioconazole against *Botrytis cinerea*, an in vitro assay was conducted using 96-well microtiter plates. The following compositions were tested:

Control (no active ingredient),
0.63 or 1.25 ppm natamycin (DSM Food Specialties, Delft, The Netherlands),
0.50 or 1.00 ppm propiconazole,
0.13 ppm prothioconazole,
0.63 ppm natamycin+1.00 ppm propiconazole,
1.25 ppm natamycin+0.50 ppm propiconazole,
1.25 ppm natamycin+0.13 ppm prothioconazole.

After filling each well of a microtiter plate with 92 µl of PCB medium, the active ingredient(s) were added from separate stock solutions prepared in PCB medium or methanol, which resulted in an intermediate volume of 100 µl per well. Subsequently, 100 µl of a *Botrytis cinerea* suspension prepared in PCB medium was used to inoculated each well with $2.5 \times 10^3$ spores/ml. Each well thus contained a final volume of 200 µl and <1% of methanol, which did not affect growth of *Botrytis cinerea* (data not shown).

After incubation of the microtiter plates for 5 and 10 days at 25° C., the in vitro antifungal activity (%) of the individual active ingredients was assessed by calculating the reduction in mould growth observed in the presence of the active ingredient in comparison to the mould growth observed in the absence of the active ingredient. The expected antifungal activity (E in %) of the active ingredient combination was calculated according to the Colby equation (Colby, 1967):

$$E = X + Y - [(X \cdot Y)/100]$$

wherein X and Y are the observed antifungal activities (in %) of the individual active ingredients X and Y, respectively. If the observed antifungal activity (O in %) of the combination exceeds the expected antifungal activity (E in %) of the combination and the resulting synergy factor O/E is thus >1.0, the combined application of the active ingredients leads to a synergistic antifungal effect.

The results (see Table 15) demonstrate that both the natamycin+propiconazole combination and the natamycin+prothioconazole combination had much stronger antifungal activities against *Botrytis cinerea* than natamycin, propiconazole or prothioconazole individually. The observed antifungal activities of the combinations natamycin+propiconazole and natamycin+prothioconazole were 50 to 100% higher than the expected antifungal activities. Consequently, synergy factors above 1.0 were obtained.

Hence, the combined application of natamycin and propiconazole as well as the combined application of natamycin and prothioconazole synergistically inhibit growth of *Botrytis cinerea*.

EXAMPLE 14

In vitro Antifungal Activity

The experiment was conducted as described in Example 13, except for the fact that the following compositions were tested:
Control (no active ingredient),
2.5 ppm natamycin (DSM Food Specialties, Delft, The Netherlands),
7.5 or 10.0 ppm propiconazole,
0.5 ppm prothioconazole,
2.5 ppm natamycin+7.5 ppm propiconazole,
2.5 ppm natamycin+10.0 ppm propiconazole,
2.5 ppm natamycin+0.5 ppm of prothioconazole.
Furthermore, *Fusarium proliferatum* was used for inoculation. The antifungal activity (in %) of the individual and combined active ingredients was determined according to the method described in Example 13.

The results (see Table 16) reveal that the active ingredient combinations natamycin+propiconazole and natamycin+prothioconazole inhibit growth of *Fusarium proliferatum* more effectively than natamycin, propiconazole or prothioconazole individually. The observed antifungal activities of the active ingredient combinations natamycin+propiconazole and natamycin+prothioconazole exceeded the expected antifungal activities with 50 to 100%, which resulted in synergy factors above 1.0.

Hence, the combined application of natamycin and propiconazole as well as the combined application of natamycin and prothioconazole displayed strong synergistic antifungal activity against *Fusarium proliferatum*.

TABLE 1

Number of moulded wounds on bananas incubated at 20° C. after treatment with compositions comprising either 500 ppm natamycin, 1000 ppm propiconazole or both.

| Antifungal composition | Number of moulded wounds/ total number of 12 wounds during incubation time (in days) | |
|---|---|---|
|  | Day 39 | Day 42 |
| Control | 12/12 | 12/12 |
| Natamycin 500 ppm | 12/12 | 12/12 |
| Propiconazole 1000 ppm | 4/12 | 4/12 |
| Natamycin 500 ppm + propiconazole 1000 ppm | 0/12 | 1/12 |

TABLE 2

Number of moulded wounds on bananas incubated at 20° C. after treatment with compositions comprising either 500 ppm natamycin, 150 ppm propiconazole or both.

| Antifungal composition | Number of moulded wounds/ total number of 12 wounds during incubation time (in days) | | |
|---|---|---|---|
|  | Day 26 | Days 27-29 | Days 31-32 |
| Control | 12/12 | 12/12 | 12/12 |
| Natamycin 500 ppm | 8/12 | 8/12 | 8/12 |
| Propiconazole 150 ppm | 9/12 | 12/12 | 12/12 |
| Natamycin 500 ppm + propiconazole 150 ppm | 0/12 | 0/12 | 1/12 |

TABLE 3

Antifungal activity (%) of compositions comprising either 500 ppm natamycin, 150 ppm propiconazole or both on bananas after incubation at 20° C.

| Antifungal composition | Incubation time (days) | Observed antifungal activity O (%) | Expected antifungal activity E (%) | Synergy factor O/E |
|---|---|---|---|---|
| Control | 27 | 0 | — | — |
| Natamycin 500 ppm |  | 81 | — | — |
| Propiconazole 150 ppm |  | 57 | — | — |
| Natamycin 500 ppm + propiconazole 150 ppm |  | 100 | 92 | 1.1 |
| Control | 28 | 0 | — | — |
| Natamycin 500 ppm |  | 81 | — | — |
| Propiconazole 150 ppm |  | 56 | — | — |
| Natamycin 500 ppm + propiconazole 150 ppm |  | 100 | 91 | 1.1 |
| Control | 29 | 0 | — | — |
| Natamycin 500 ppm |  | 81 | — | — |
| Propiconazole 150 ppm |  | 54 | — | — |
| Natamycin 500 ppm + propiconazole 150 ppm |  | 100 | 91 | 1.1 |
| Control | 31 | 0 | — | — |
| Natamycin 500 ppm |  | 74 | — | — |
| Propiconazole 150 ppm |  | 44 | — | — |
| Natamycin 500 ppm + propiconazole 150 ppm |  | 99 | 85 | 1.2 |
| Control | 32 | 0 | — | — |
| Natamycin 500 ppm |  | 72 | — | — |
| Propiconazole 150 ppm |  | 33 | — | — |
| Natamycin 500 ppm + propiconazole 150 ppm |  | 99 | 81 | 1.2 |

TABLE 4

Number of moulded wounds on bananas incubated at 20° C. after treatment with compositions comprising either 250 ppm natamycin, 500 ppm propiconazole or both.

| Antifungal composition | Number of moulded wounds/ total number of 12 wounds during incubation time (in days) | |
|---|---|---|
|  | Day 34 | Day 36 |
| Control | 12/12 | 12/12 |
| Natamycin 250 ppm | 12/12 | 12/12 |
| Propiconazole 500 ppm | 10/12 | 10/12 |
| Natamycin 250 ppm + propiconazole 500 ppm | 7/12 | 8/12 |

TABLE 5

Antifungal activity (%) of compositions comprising either 250 ppm natamycin, 500 ppm propiconazole or both on bananas after incubation at 20° C.

| Antifungal composition | Incubation time (days) | Observed antifungal activity O (%) | Expected antifungal activity E (%) | Synergy factor O/E |
|---|---|---|---|---|
| Control | 34 | 0 | — | — |
| Natamycin 250 ppm | | 0 | — | — |
| Propiconazole 500 ppm | | 74 | — | — |
| Natamycin 250 ppm + propiconazole 500 ppm | | 85 | 74 | 1.1 |
| Control | 36 | 0 | — | — |
| Natamycin 250 ppm | | 0 | — | — |
| Propiconazole 500 ppm | | 62 | — | — |
| Natamycin 250 ppm + propiconazole 500 ppm | | 83 | 62 | 1.3 |
| Control | 39 | 0 | — | — |
| Natamycin 250 ppm | | 0 | — | — |
| Propiconazole 500 ppm | | 43 | — | — |
| Natamycin 250 ppm + propiconazole 500 ppm | | 75 | 43 | 1.7 |
| Control | 42 | 0 | — | — |
| Natamycin 250 ppm | | 0 | — | — |
| Propiconazole 500 ppm | | 33 | — | — |
| Natamycin 250 ppm + propiconazole 500 ppm | | 71 | 33 | 2.2 |

TABLE 6

Antifungal activity (%) of compositions comprising either 250 ppm natamycin, 50 ppm propiconazole or both on bananas after incubation at 20° C.

| Antifungal composition | Incubation time (days) | Observed antifungal activity O (%) | Expected antifungal activity E (%) | Synergy factor O/E |
|---|---|---|---|---|
| Control | 23 | 0 | — | — |
| Natamycin 250 ppm | | 23 | — | — |
| Propiconazole 50 ppm | | 36 | — | — |
| Natamycin 250 ppm + propiconazole 50 ppm | | 59 | 51 | 1.2 |
| Control | 27 | 0 | — | — |
| Natamycin 250 ppm | | 26 | — | — |
| Propiconazole 50 ppm | | 30 | — | — |
| Natamycin 250 ppm + propiconazole 50 ppm | | 66 | 48 | 1.4 |
| Control | 29 | 0 | — | — |
| Natamycin 250 ppm | | 29 | — | — |
| Propiconazole 50 ppm | | 35 | — | — |
| Natamycin 250 ppm + propiconazole 50 ppm | | 69 | 53 | 1.3 |

TABLE 7

Number of moulded wounds on bananas incubated at 20° C. after treatment with compositions comprising either 50 ppm natamycin, 250 ppm propiconazole or both.

| | Number of moulded wounds/ total number of 12 wounds during incubation time (in days) | | | | | |
|---|---|---|---|---|---|---|
| Antifungal composition | Day 29 | Day 32 | Day 34 | Day 36 | Day 39 | Day 42 |
| Control | 12/12 | 12/12 | 12/12 | 12/12 | 12/12 | 12/12 |
| Natamycin 50 ppm | 12/12 | 12/12 | 12/12 | 12/12 | 12/12 | 12/12 |
| Propiconazole 250 ppm | 5/12 | 8/12 | 10/12 | 12/12 | 12/12 | 12/12 |
| Natamycin 50 ppm + propiconazole 250 ppm | 0/12 | 2/12 | 4/12 | 5/12 | 8/12 | 10/12 |

TABLE 8

Antifungal activity (%) of compositions comprising either 50 ppm natamycin, 250 ppm propiconazole or both on bananas after incubation at 20° C.

| Antifungal composition | Incubation time (days) | Observed antifungal activity O (%) | Expected antifungal activity E (%) | Synergy factor O/E |
|---|---|---|---|---|
| Control | 29 | 0 | — | — |
| Natamycin 50 ppm | | 4 | — | — |
| Propiconazole 250 ppm | | 92 | — | — |
| Natamycin 50 ppm + propiconazole 250 ppm | | 100 | 93 | 1.1 |
| Control | 32 | 0 | — | — |
| Natamycin 50 ppm | | 1 | — | — |
| Propiconazole 250 ppm | | 90 | — | — |
| Natamycin 50 ppm + propiconazole 250 ppm | | 97 | 90 | 1.1 |
| Control | 34 | 0 | — | — |
| Natamycin 50 ppm | | 1 | — | — |
| Propiconazole 250 ppm | | 85 | — | — |
| Natamycin 50 ppm + propiconazole 250 ppm | | 95 | 85 | 1.1 |
| Control | 36 | 0 | — | — |
| Natamycin 50 ppm | | 0 | — | — |
| Propiconazole 250 ppm | | 81 | — | — |
| Natamycin 50 ppm + propiconazole 250 ppm | | 94 | 81 | 1.2 |
| Control | 39 | 0 | — | — |
| Natamycin 50 ppm | | 0 | — | — |
| Propiconazole 250 ppm | | 57 | — | — |
| Natamycin 50 ppm + propiconazole 250 ppm | | 87 | 57 | 1.5 |
| Control | 42 | 0 | — | — |
| Natamycin 50 ppm | | 0 | — | — |
| Propiconazole 250 ppm | | 47 | — | — |
| Natamycin 50 ppm + propiconazole 250 ppm | | 84 | 47 | 1.8 |

TABLE 9

Number of moulded wounds on bananas incubated at 20° C. after treatment with compositions comprising either 500 ppm natamycin, 250 ppm prothioconazole or both.

| Antifungal composition | Number of moulded wounds/ total number of 12 wounds during incubation time (in days) Day 27, 28 and 29 |
|---|---|
| Control | 12/12 |
| Natamycin 500 ppm | 8/12 |
| Prothioconazole 250 ppm | 10/12 |
| Natamycin 500 ppm + prothioconazole 250 ppm | 2/12 |

TABLE 10

Number of moulded wounds on bananas incubated at 20° C. after treatment with compositions comprising either 250 ppm natamycin, 100 ppm prothioconazole or both.

| | Number of moulded wounds/ total number of 12 wounds during incubation time (in days) | |
|---|---|---|
| Antifungal composition | Day 27 | Day 28 and 29 |
| Control | 12/12 | 12/12 |
| Natamycin 250 ppm | 12/12 | 12/12 |
| Prothioconazole 100 ppm | 11/12 | 12/12 |
| Natamycin 250 ppm + prothioconazole 100 ppm | 9/12 | 9/12 |

TABLE 11

Number of moulded strawberries incubated at 20° C. after treatment with compositions comprising either 250 ppm natamycin, 500 ppm prothioconazole or both.

| Antifungal composition | Number of moulded wounds/total number of 12 wounds during incubation time (in days) | |
|---|---|---|
| | Day 2 | Day 3 |
| Control | 12/12 | 12/12 |
| Natamycin 250 ppm | 10/12 | 12/12 |
| Prothioconazole 500 ppm | 12/12 | 12/12 |
| Natamycin 250 ppm + prothioconazole 500 ppm | 6/12 | 8/12 |

TABLE 12

Antifungal activity (%) of compositions comprising either 250 ppm natamycin, 500 ppm prothioconazole or both on strawberries after incubation at 20° C.

| Antifungal composition | Incubation time (days) | Observed antifungal activity O (%) | Expected antifungal activity E (%) | Synergy factor O/E |
|---|---|---|---|---|
| Control | 2 | 0 | — | — |
| Natamycin 250 ppm | | 31 | — | — |
| Prothioconazole 500 ppm | | 14 | — | — |
| Natamycin 250 ppm + prothioconazole 500 ppm | | 55 | 41 | 1.4 |
| Control | 3 | 0 | — | — |
| Natamycin 250 ppm | | 24 | — | — |
| Prothioconazole 50 ppm | | 21 | — | — |
| Natamycin 250 ppm + prothioconazole 500 ppm | | 50 | 40 | 1.2 |

TABLE 13

Antifungal activity (%) of compositions comprising either 500 ppm natamycin, 600 ppm prothioconazole or both on mandarins after incubation at 20° C.

| Antifungal composition | Incubation time (days) | Observed antifungal activity O (%) | Expected antifungal activity E (%) | Synergy factor O/E |
|---|---|---|---|---|
| Control | 25 | 0 | — | — |
| Natamycin 500 ppm | | 34 | — | — |
| Prothioconazole 600 ppm | | 91 | — | — |
| Natamycin 500 ppm + prothioconazole 600 ppm | | 100 | 94 | 1.1 |
| Control | 28 | 0 | — | — |
| Natamycin 500 ppm | | 27 | — | — |
| Prothioconazole 600 ppm | | 83 | — | — |
| Natamycin 500 ppm + prothioconazole 600 ppm | | 100 | 88 | 1.1 |
| Control | 31 | 0 | — | — |
| Natamycin 500 ppm | | 24 | — | — |
| Prothioconazole 600 ppm | | 71 | — | — |
| Natamycin 500 ppm + prothioconazole 600 ppm | | 100 | 78 | 1.3 |
| Control | 34 | 0 | — | — |
| Natamycin 500 ppm | | 24 | — | — |
| Prothioconazole 600 ppm | | 63 | — | — |
| Natamycin 500 ppm + prothioconazole 600 ppm | | 100 | 72 | 1.4 |

TABLE 14

Antifungal activity (%) of compositions comprising either 250 ppm natamycin, 150 ppm prothioconazole or both on mandarins after incubation at 20° C.

| Antifungal composition | Incubation time (days) | Observed antifungal activity O (%) | Expected antifungal activity E (%) | Synergy factor O/E |
|---|---|---|---|---|
| Control | 13 | 0 | — | — |
| Natamycin 250 ppm | | 27 | — | — |
| Prothioconazole 150 ppm | | 86 | — | — |
| Natamycin 250 ppm + prothioconazole 150 ppm | | 100 | 90 | 1.1 |
| Control | 16 | 0 | — | — |
| Natamycin 250 ppm | | 15 | — | — |
| Prothioconazole 150 ppm | | 82 | — | — |
| Natamycin 250 ppm + prothioconazole 150 ppm | | 100 | 85 | 1.2 |
| Control | 21 | 0 | — | — |
| Natamycin 250 ppm | | 6 | — | — |
| Prothioconazole 150 ppm | | 71 | — | — |
| Natamycin 250 ppm + prothioconazole 150 ppm | | 100 | 73 | 1.4 |
| Control | 26 | 0 | — | — |
| Natamycin 250 ppm | | 5 | — | — |
| Prothioconazole 150 ppm | | 63 | — | — |
| Natamycin 250 ppm + prothioconazole 150 ppm | | 93 | 65 | 1.4 |
| Control | 29 | 0 | — | — |
| Natamycin 250 ppm | | 3 | — | — |
| Prothioconazole 150 ppm | | 40 | — | — |
| Natamycin 250 ppm + prothioconazole 150 ppm | | 77 | 42 | 1.8 |
| Control | 34 | 0 | — | — |
| Natamycin 250 ppm | | 0 | — | — |
| Prothioconazole 150 ppm | | 27 | — | — |
| Natamycin 250 ppm + prothioconazole 150 ppm | | 65 | 27 | 2.4 |

TABLE 15

In vitro antifungal activity (%) of natamycin in combination with propiconazole or prothioconazole against *Botrytis cinerea* after incubation at 25° C.

| Antifungal composition | Incubation time (days) | Observed antifungal activity O (%) | Expected antifungal activity E (%) | Synergy factor O/E |
|---|---|---|---|---|
| Control | 5 | 0 | — | — |
| Natamycin 0.63 ppm | | 0 | — | — |
| Natamycin 1.25 ppm | | 0 | — | — |
| Propiconazole 0.50 ppm | | 0 | — | — |
| Propiconazole 1.00 ppm | | 0 | — | — |
| Prothioconazole 0.13 ppm | | 0 | — | — |
| Natamycin 0.63 ppm + Propiconazole 1.00 ppm | | 100 | 0 | >100 |
| Natamycin 1.25 ppm + Propiconazole 0.50 ppm | | 100 | 0 | >100 |
| Natamycin 1.25 ppm + Prothioconazole 0.13 ppm | | 100 | 0 | >100 |
| Control | 10 | 0 | — | — |
| Natamycin 1.25 ppm | | 0 | — | — |
| Prothioconazole 0.13 ppm | | 50 | — | — |
| Natamycin 1.25 ppm + Prothioconazole 0.13 ppm | | 100 | 50 | 2.0 |

TABLE 16

In vitro antifungal activity (%) of natamycin in combination with propiconazole or prothioconazole against *Fusarium proliferatum* after incubation at 25° C.

| Antifungal composition | Incubation time (days) | Observed antifungal activity O (%) | Expected antifungal activity E (%) | Synergy factor O/E |
|---|---|---|---|---|
| Control | 3 | 0 | — | — |
| Natamycin 2.5 ppm | | 0 | — | — |
| Propiconazole 7.5 ppm | | 0 | — | — |
| Propiconazole 10.0 ppm | | 0 | — | — |
| Natamycin 2.5 ppm + Propiconazole 7.5 ppm | | 50 | 0 | >50 |
| Natamycin 2.5 ppm + Propiconazole 10.0 ppm | | 100 | 0 | >100 |
| Control | 10 | 0 | — | — |
| Natamycin 2.5 ppm | | 0 | — | — |
| Prothioconazole 0.5 ppm | | 50 | — | — |
| Natamycin 2.5 ppm + Prothioconazole 0.5 ppm | | 100 | 0 | 2.0 |

REFERENCES

Buchenauer H (1987), DMI fungicide: Side effects on the plant and problems of resistance. Pages 259-290 in: Modern Selective Fungicides, 2nd Edn. H. Lyr, ed. Gustav Fisher Verlag, Jena, Germany.

Colby S R (1967), Calculating synergistic and antagonistic responses of herbicide combination. Weeds 15: 20-22.

Kuck K H, Scheinpflug H and Pontzen R (1987), DMI fungicides. Pages 205-258 in: Modern Selective Fungicides, 2nd Edn. H. Lyr, ed. Gustav Fisher Verlag, Jena, Germany.

Lapeyre de Bellaire de L and Dubois C (1987), Distribution of Thiabendazole-Resistant *Colletotrichum musae* Isolates from Guadeloupe Banana Plantations. Plant Disease 81:1378-1383.

Ma Z, Morgan D P, Felts D and Michailides T J (2002), Sensitivity of *Botryosphaeria dothidea* from California pistachio to tebuconazole. Crop Prot. 21:829-835.

Slinker B K (1998), The Statistics of Synergism. Journal of Mol. and Cell. Cardiology 30:723-731.

The invention claimed is:

1. A composition comprising natamycin and at least one antifungal compound from the family of triazole fungicides selected from the group consisting of amisulbrom, azaconazole, bitertanol, bromuconazole, cyproconazole, diclobutrazol, difenoconazole, diniconazole, diniconazole-M, etaconazole, fenbuconazole, fluotrimazole, fluquinconazole, flusilazole, flutriafol, furconazole, furconazole-cis, hexaconazole, huanjunzuo, imibenconazole, ipconazole, myclobutanil, penconazole, propiconazole, prothioconazole, quinconazole, simeconazole, tebuconazole, tetraconazole, triazbutil, triticonazole, uniconazole and uniconazole-P.

2. A composition according to claim 1, wherein the composition further comprises at least one additional compound selected from the group consisting of a sticking agent, a carrier, a colouring agent, a protective colloid, an adhesive, a herbicide, a fertilizer, a thickening agent, a sequestering agent, a thixotropic agent, a surfactant, a further antimicrobial compound, a detergent, a preservative, a spreading agent, a filler, a spray oil, a flow additive, a mineral substance, a solvent, a dispersant, an emulsifier, a wetting agent, a stabiliser, an antifoaming agent, a buffering agent, an UV-absorber and an antioxidant.

3. A composition according to claim 1, wherein the amount of natamycin is in a range from 0.005 g/l to about 100 g/l and the amount of the at least one antifungal compound from the family of triazole fungicides is in a range from about 0.0001 g/l to about 2000 g/l.

4. A kit comprising natamycin and at least one antifungal compound from the family of triazole fungicides selected from the group consisting of amisulbrom, azaconazole, bitertanol, bromuconazole, cyproconazole, diclobutrazol, difenoconazole, diniconazole, diniconazole-M, etaconazole, fenbuconazole, fluotrimazole, fluquinconazole, flusilazole, flutriafol, furconazole, furconazole-cis, hexaconazole, huanjunzuo, imibenconazole, ipconazole, myclobutanil, penconazole, propiconazole, prothioconazole, quinconazole, simeconazole, tebuconazole, tetraconazole, triazbutil, triticonazole, uniconazole and uniconazole-P.

5. A method for protecting a product against fungi by treating the product with natamycin and at least one antifungal compound from the family of triazole fungicides selected from the group consisting of amisulbrom, azaconazole, bitertanol, bromuconazole, cyproconazole, diclobutrazol, difenoconazole, diniconazole, diniconazole-M, etaconazole, fenbuconazole, fluotrimazole, fluquinconazole, flusilazole, flutriafol, furconazole, furconazole-cis, hexaconazole, huanjunzuo, imibenconazole, ipconazole, myclobutanil, penconazole, propiconazole, prothioconazole, quinconazole, simeconazole, tebuconazole, tetraconazole, triazbutil, triticonazole, uniconazole and uniconazole-P.

6. A method according to claim 5, wherein the product is treated with a composition comprising natamycin and said at least one antifungal compound.

7. A method according to claim 5, wherein the product is at least one selected from the group consisting of a food product, a feed product, a pharmaceutical product, a cosmetic product and an agricultural product.

8. A method according to claim 6, wherein the product is an agricultural product.

9. A method according to claim 7, wherein the product is treated post-harvest.

10. A product comprising natamycin and at least one antifungal compound from the family of triazole fungicides selected from the group consisting of amisulbrom, azaconazole, bitertanol, bromuconazole, cyproconazole, diclobutrazol, difenoconazole, diniconazole, diniconazole-M, etaconazole, fenbuconazole, fluotrimazole, fluquinconazole, flusilazole, flutriafol, furconazole, furconazole-cis, hexaconazole, huanjunzuo, imibenconazole, ipconazole, myclobutanil, penconazole, propiconazole, prothioconazole, quinconazole, simeconazole, tebuconazole, tetraconazole, triazbutil, triticonazole, uniconazole and uniconazole-P.

11. A product according to claim 10, wherein the product is at least one selected from the group consisting of a food product, a feed product, a pharmaceutical product, a cosmetic product and an agricultural product.

12. A product according to claim 10, wherein the product is an agricultural product.

* * * * *